(12) United States Patent
Vargas Fonseca

(10) Patent No.: US 12,005,176 B2
(45) Date of Patent: Jun. 11, 2024

(54) METHOD FOR RECOVERING RESIDUAL BLOOD FROM AN EXTRACORPOREAL CIRCULATION CIRCUIT AND EQUIPMENT FOR COLLECTING AND RECOVERING RESIDUAL BLOOD IN THE EXTRACORPOREAL CIRCULATION CIRCUIT

(71) Applicant: ZAMMI INSTRUMENTAL LTDA, Duque de Caxias (BR)

(72) Inventor: Luiz Henrique Vargas Fonseca, Duque de Caxias (BR)

(73) Assignee: ZAMMI INSTRUMENTAL LTDA, Duque de Caxias (BR)

( * ) Notice: Subject to any disclaimer, the term of this patent is extended or adjusted under 35 U.S.C. 154(b) by 464 days.

(21) Appl. No.: 16/753,655

(22) PCT Filed: Sep. 12, 2018

(86) PCT No.: PCT/BR2018/050336
§ 371 (c)(1),
(2) Date: Jul. 28, 2020

(87) PCT Pub. No.: WO2019/068158
PCT Pub. Date: Apr. 11, 2019

(65) Prior Publication Data
US 2020/0353152 A1 Nov. 12, 2020

(30) Foreign Application Priority Data

Oct. 6, 2017 (BR) .......................... 102017021552-0

(51) Int. Cl.
*A61M 1/36* (2006.01)
*A61M 1/34* (2006.01)

(52) U.S. Cl.
CPC ............ *A61M 1/3646* (2014.02); *A61M 1/34* (2013.01); *A61M 1/3403* (2014.02);
(Continued)

(58) Field of Classification Search
CPC .. A61M 1/3646; A61M 1/3403; A61M 1/341; A61M 1/3666; A61M 1/34;
(Continued)

(56) References Cited

U.S. PATENT DOCUMENTS 4,828,543 A 5/1989 Weiss
5,651,765 A * 7/1997 Haworth .............. B01D 29/012
210/493.1

(Continued)

FOREIGN PATENT DOCUMENTS

CN 105889532 A * 8/2016
JP 2017520312 A * 7/2017
(Continued)

OTHER PUBLICATIONS

Machine generated translation of JP 2017520312 A (Year: 2017).*
Machine generated translation of CN-105889532-A (Year: 2016).*

*Primary Examiner* — Magali P Slawski
*Assistant Examiner* — Bernadette Karen McGann
(74) *Attorney, Agent, or Firm* — RAPHAEL BELLUM PLLC

(57) ABSTRACT

The processes and equipment for collecting and recovering residual blood from cardiopulmonary bypass provide increased efficiency in hemoconcentrators and hemodialysers. Residual blood collection and recovery equipment for extracorporeal circulation circuits include a flow-limiting valve disposed at an exit of a hemofilter, which automatically regulates a resistance in a line as a function of an inlet pressure. The valves of the residual blood collection and recovery equipment also include an opening that is propor- (Continued)

tional to a flow and a hematocrit. The systems and methods for blood recovery can be used after surgery or for hemodialysis, in addition to other applications.

6 Claims, 12 Drawing Sheets

(52) U.S. Cl.
CPC ........... *A61M 1/3601* (2014.02); *A61M 1/341* (2014.02); *A61M 1/3666* (2013.01); *A61M 2205/3331* (2013.01); *A61M 2230/207* (2013.01)

(58) Field of Classification Search
CPC ........ A61M 1/3601; A61M 2205/3331; A61M 2230/207
See application file for complete search history.

(56) References Cited

U.S. PATENT DOCUMENTS

| | | | |
|---|---|---|---|
| 6,607,386 B1* | 8/2003 | Andersson | A61C 5/77 433/201.1 |
| 2003/0135152 A1 | 7/2003 | Kollar | |
| 2010/0187176 A1* | 7/2010 | Del Canizo Lopez | A61M 60/113 210/219 |
| 2017/0350529 A1* | 12/2017 | Vargas Fonseca | F16K 17/16 |

FOREIGN PATENT DOCUMENTS

| | | |
|---|---|---|
| WO | 2015179929 A1 | 3/2015 |
| WO | 2016090438 A1 | 6/2016 |

\* cited by examiner

METHOD FOR RECOVERING RESIDUAL BLOOD FROM AN EXTRACORPOREAL CIRCULATION CIRCUIT AND EQUIPMENT FOR COLLECTING AND RECOVERING RESIDUAL BLOOD IN THE EXTRACORPOREAL CIRCULATION CIRCUIT

FIELD OF THE INVENTION

The present invention deals with a new process and equipment for collecting and recovering residual blood from cardiopulmonary bypass, notably with the purpose of increasing efficiency in hemoconcentrators and hemodialysers. The present invention is advantageously employed, especially, for blood recovery after surgery or for hemodialysis, in addition to other applications employing this technique.

BACKGROUND OF THE INVENTION

Cardiovascular surgeries using cardiopulmonary bypass (CPB) represent an important burden on the blood bank stocks, since several factors related to CPB lead to a high consumption of blood products. In the United States, cardiac surgery consumes 15 to 20% of all blood products transfused. Homologous (or allogenic) blood product transfusions are associated with increased postoperative mortality. In addition, homologous transfusion is one of the main vehicles for the transmission of pathogens, such as hepatitis C virus and HIV.

In the first cardiac surgeries, about 3 to 5 liters of blood were used to start each procedure, thus, filling the CPB circuit worked as a large homologous blood transfusion, and with all its troublesomeness. The demand for blood use meant an enormous burden on blood banks and, consequently, caused a limitation on the number of surgeries and mainly affected patients with the rarest blood groups.

Upon the introduction of hemodilution as an alternative to blood priming, there has been a reduction in homologous transfusions, in addition to attenuating the adverse effects of blood perfusion, especially homologous blood syndrome. Hemodilution brought several benefits of acellular perfusate, such as reduced blood viscosity and improved tissue perfusion, however, excessive hemodilution can jeopardize oxygen transport and results in the need for perioperative transfusion. Hemodilution is associated with significant mortality, especially when the hematocrit reaches values below 20%. The control of excessive hemodilution led to the adoption of new measures to lessen its negative effects and, at the same time, to reduce the use of homologous blood in the cardiac surgery perioperative period. Among the solutions introduced for reducing perioperative transfusion, the recovery of blood losses using cell savers, the use of mini-CPB circuits and ultrafiltration were those with the best levels of evidence.

The cell washer uses the spin method as working principle. In this procedure, blood undergoes centrifugation at a speed of 4,000 to 6,000 rotations per minute (RPM), for at least 5 minutes. The final product of the processing is a concentrate of washed red cells, and the other blood components of the plasma are discarded during the process. The impact of red blood cell recovery from blood losses has both positive and negative aspects. The increase in red blood cell, hematocrit and hemoglobin concentrations in the perioperative period as well as removal of contaminants from the blood are among the positive aspects. Among the negative aspects of using cell washer, despite the level of evidence, is the fact that its indication is not consensual and its cost-effectiveness is questionable as this model does not effectively reduce the homologous transfusion, and furthermore the level of mechanical stress caused by centrifugation causes blood hemolysis.

The ultrafiltration is the use of a semipermeable membrane capable of allowing the passage of water and electrolytes through its pores, while the blood cell, protein and high molecular weight substances do not cross the membrane and remain in circulation. Ultrafiltration is a procedure widely performed in cardiac surgery with the purpose of controlling excessive hemodilution during cardiopulmonary bypass. Some authors allege that ultrafiltration can remove inflammatory chemical mediators. In addition to plasma water, the membrane allows the passage of small molecules with a molecular weight between 20,000 to 30,000 Daltons (Da), according to the type of membrane. Ultrafiltration performed during cardiopulmonary bypass has become acknowledged as conventional ultrafiltration, however there are other modified techniques of applying ultrafiltration during and after cardiopulmonary bypass. The result of ultrafiltration blood processing is the concentration of whole blood with all its constituent elements. Hemoconcentration is more advantageous for blood recovery in the cardiac surgery perioperative period than processes employing centrifugation, however, there is still no standardized technique that effectively controls the efficiency and safety of the process.

The residual blood from the circuit at the end of the CPB is usually very diluted, often with hematocrit below 20%, or approximately 44% of the normal hematocrit value (40 to 45%), in addition, patients immediately after CPB often do not tolerate or do not resist the entire volume of blood that remains in the CPB circuit, and, frequently, the final volume of residual blood in the circuit can surpass 2,000 mL. Considering this post-CPB scenario, the patient does not tolerate the immediate passage of all blood that remained in the circuit; however, he/she is anemic due to hemodilution, which can threaten his/her clinical condition and further require a homologous transfusion. The residual volume can be concentrated, the excess plasma water can be removed, and a smaller volume of blood concentrated or just restored.

The hemofilter of the state of the art is composed of hollow fibers made of a type of membrane whose porosity allows the passage of water and other components of the blood plasma through its pores whilst preventing blood passage. These fibers are arranged inside a rigid casing, having connectors axially arranged for blood inflow and outflow, which passes through the fibers and connectors, laterally arranged on the outside of the casing so as to allow filtrate outflow, which crosses the membrane pores.

The distribution of the resistance which blood flow undergoes in crossing the hemofilter, allows both blood and water to pass through direct resistance, wherein only water passes through the transmembrane resistance. In the circuits currently used, hemofilter inlet and outlet tubes are the same, therefore, the resistance to flow passage inside the hollow fibers (direct resistance) is lower than the resistance to flow passage through the membrane pores (transmembrane resistance). Therefore, for the filtration to occur, i.e. for the water contained in the blood to pass through the membrane, a high flow is required to generate high pressure. As an example, by using a normal hemofilter, about 15 mL/min of filtrate is possible to collect, subjecting the filter to a flow rate of 300 mL/min, i.e., the volume filtered represents only 5% of the total volume crossing the hemofilter.

In view of the above, it is concluded that if the direct resistance is proportionally increased, it would be easier for water to pass through the membrane. This resistance increase can be achieved by introducing an additional resistance after, for example, the dialyzer. This additional resistance can be obtained in several ways, for example, by placing a smaller gauge tube at the filter outlet, or even partially occluding the outlet tube. By doing this procedure, it is likely to obtain a higher percentage of filtrate, however, some limitations and risks would be generated as the pressure through the filter varies according to the flow and also to the hematocrit, since the higher the hematocrit, the greater the viscosity of the blood. In this way, not only the filtration percentage varies, but also the transmembrane pressure. If transmembrane pressure needs to be controlled during the process, with higher hematocrit and/or flow, the transmembrane pressure can become higher and cause damage to the membrane and blood. Thus, we came to the conclusion that in order to safely increase the efficiency of the hemofilter, it would be necessary to develop a method and equipment capable of controlling the additional resistance at the hemofilter outlet as a function of the transmembrane pressure, in order to maintain the highest possible resistance, provided that the value of the transmembrane pressure is within the safety limit of the filter, which usually varies between 500 and 600 mmHg.

Therefore, the objective of the present invention is to provide an improved process and equipment for performing hemofiltration, which provides the recovery of blood from the patient bringing together high quality and high efficiency while avoiding problems of rupture of the hemofilter membrane and destruction of the blood being recovered, such as occurs in the devices of the state of the art currently available on the world market.

BRIEF DESCRIPTION OF THE FIGURES

The procedure and equipment for collecting and recovering residual blood from cardiopulmonary bypass, object of the present invention, will be hereinafter described with reference to the appended figures, which, diagrammatically, and not limiting its scope, represent.

DETAILED DESCRIPTION OF THE INVENTION

Figure 1:
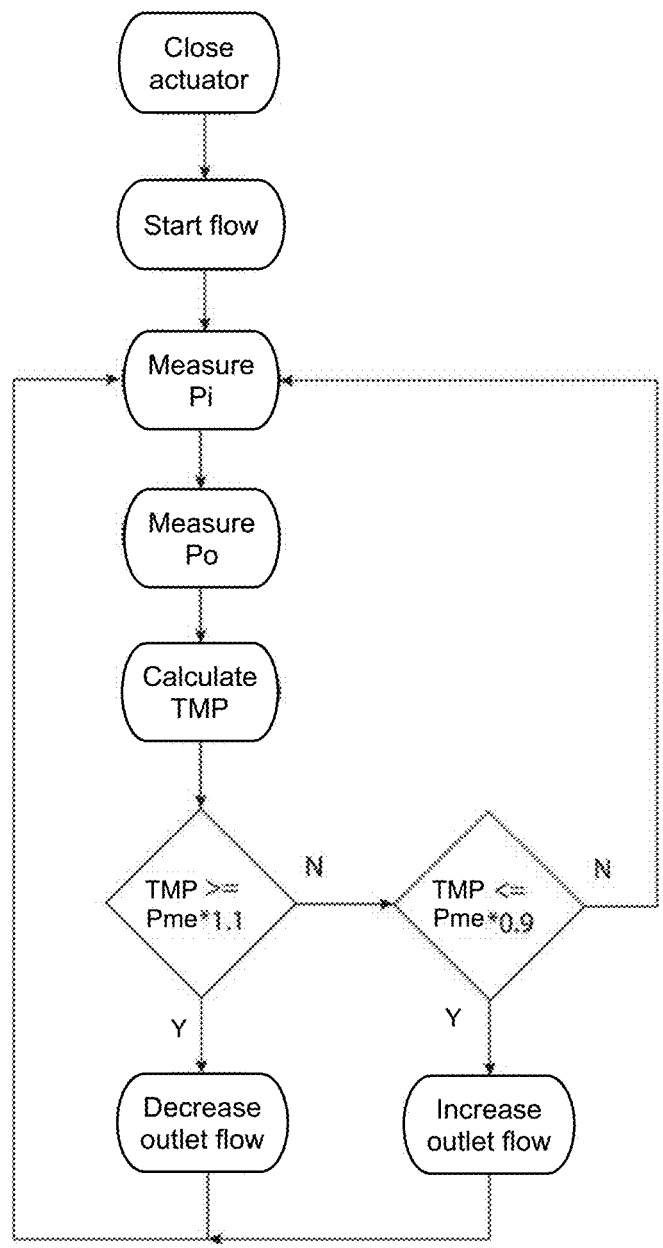
FIG. 1—illustrates the block diagram of the blood recovery process according to the present invention.
Figure 2:
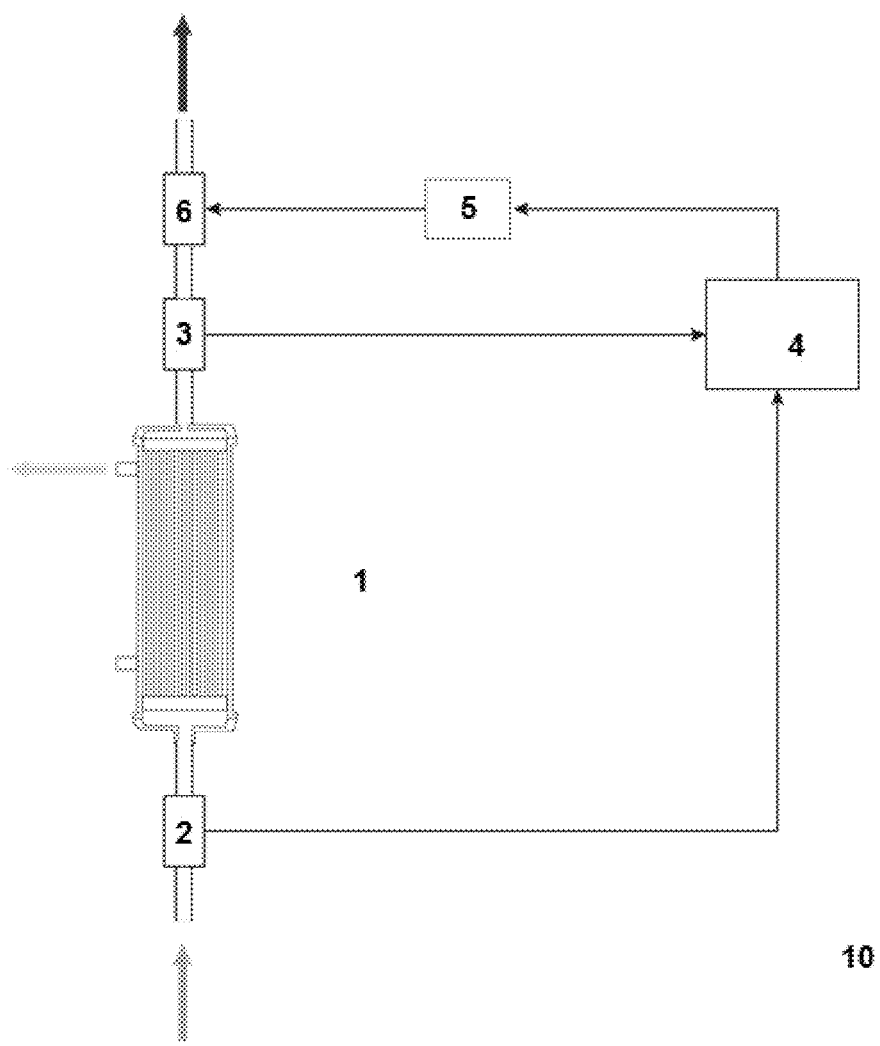
FIG. 2—illustrates a scheme of a blood recovery equipment according to the present invention.

The basic process for blood recovery, according to the present invention, is illustrated in FIGS. 1 and 2, the latter representing a diagram of the blood circuit. Accordingly, the blood recovery process is based on and implemented according to the steps of the algorithm in FIG. 1, grounded on the formula below:

$$TPM = \frac{Pi + Po}{2} + Pn$$

wherein:
TMP=transmembrane pressure (mmHg)
Pi=hemoconcentrator inlet blood pressure (mmHg)
Po=hemoconcentrator outlet blood pressure (mmHg)
Pn=value of the negative pressure applied to the ultrafilter effluent (mmHg)—considered as zero for the implemented process
Pme=maximum efficiency transmembrane pressure, defined by the user.

To implement the process, as illustrated in FIG. 2, an equipment (10) is provided comprising a hemofilter (1) having, at one end thereof, an inlet pressure sensor (2) and an outlet pressure sensor (3), said pressure sensor (2) is located at the inlet of the hemofilter (1) and said pressure sensor (3) is located at the outlet of the hemofilter (1), the pressure sensors (2, 3) are interconnected to the CPU (4), wherein the CPU (4) is connected to an actuator (5), the equipment (10) further comprises a flow controller (6) that is interconnected to the actuator (5). The equipment (10) must be filled with serum and the outflow controller (6), fully closed. Thus, when the blood flow is initiated, blood begins to enter the hemofilter (1) and as the flow controller (6) is closed, it accumulates inside the hemofilter (1). Meanwhile, the serum that filled the hemofilter (1) is being pushed by the blood that enters and starts to leave the pores of the membrane, until the hemofilter (1) is completely filled with blood. At this moment, the internal pressure inside the filter begins to increase and when the TMP reaches the value defined by the user, the equipment (10) begins to gradually open the flow controller (6), in order to keep the TMP equal to the defined value. From this point on, since there is no blood recirculation and the incoming blood is always in the same condition, the equipment (10) is in balance until the end of the process.

The filtration efficiency depends on the defined TMP value, the inlet flow and the hematocrit and can be calculated by the following equation:

Ef=(Fv/Bv)*100 wherein:
Ef=% filtration efficiency
Fv=filtrate volume
Bv=blood volume
or even by the equation Ef=((If−Of)/If)*100 wherein:
Ef=% filtration efficiency
If=inlet flow
Of=outlet flow

Therefore, since the equipment of the present invention provides means for measuring the inlet flow and outlet flow using the above equation, it is possible to continuously calculate the filtration efficiency and control it in real-time. This is a feature that has never seen before in the prior art devices and systems for recovering residual blood from cardiopulmonary bypass.

Figure 3:
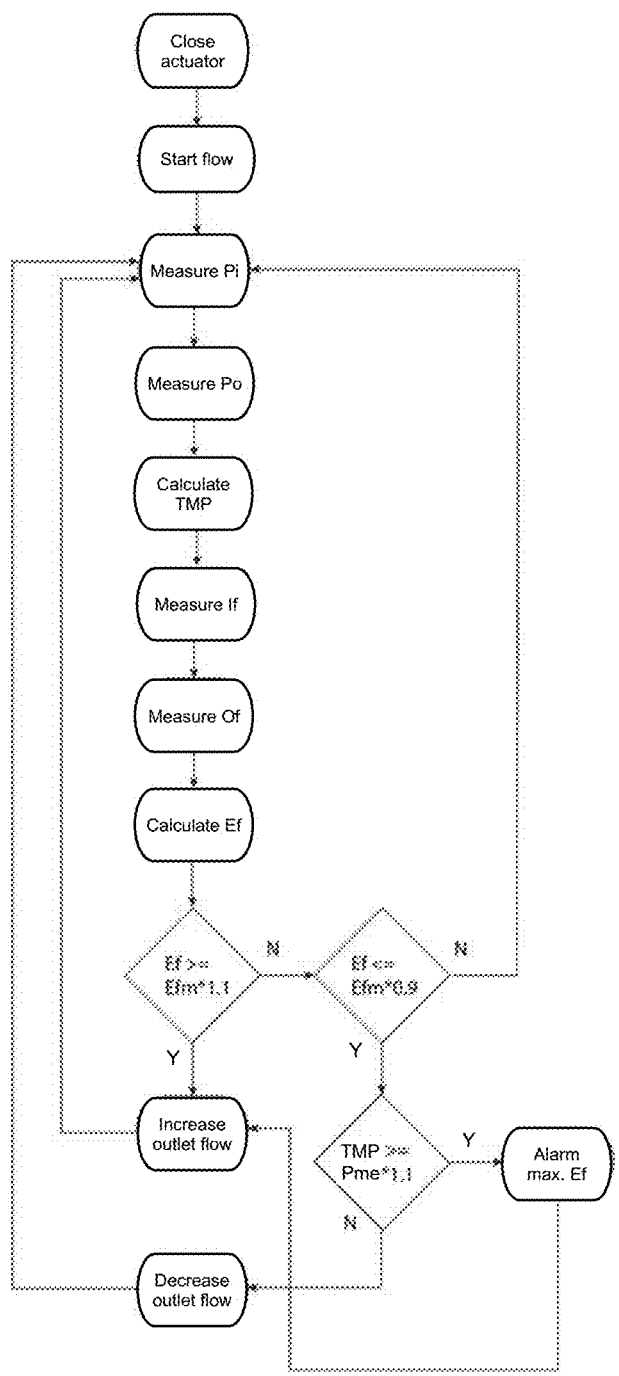
FIG. 3—illustrates a block diagram of a first embodiment of the blood recovery process according to the present invention.
Figure 4:
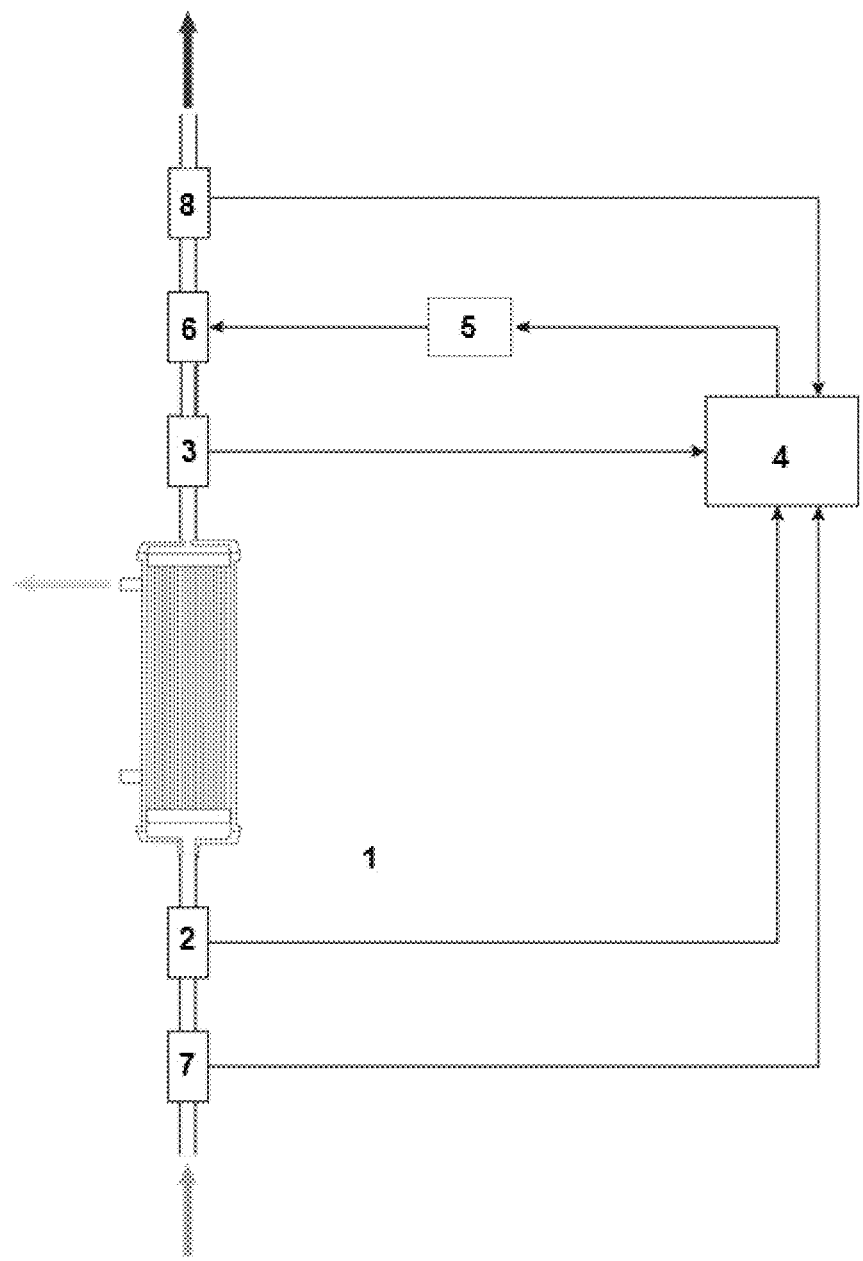
FIG. 4—illustrates a scheme of a first embodiment of the equipment according to the present invention.

Additionally, a better result can still be achieved by the process and equipment illustrated, respectively, in FIGS. 3 and 4.

Considering the process based on the algorithm of FIG. 3 and the respective equipment (20) comprising all the elements of the equipment (10) as well as the arrangement of the same components, in addition to the equipment (20) also including flow sensors (7) and (8), wherein the flow sensor (7) is connected to the pressure sensor (2) and a flow sensor (8) is connected to the flow controller (6), additionally, the flow sensors (7) and (8) are interconnected to the CPU (4), one may define the efficiency intended to be obtained by the process, the maximum TMP, and the inlet flow. Said equipment (20) is illustrated by FIG. 4. Thus, the system is in charge of setting the process parameters, including the inlet flow, so as to obtain the efficiency defined by the user and keep the TMP within the safety limits of the filter. In case the desired efficiency with the adjusted flow is not possible to obtain, the system will emit an alarm informing that the achievement of the desired efficiency is not possible.

Figure 5:
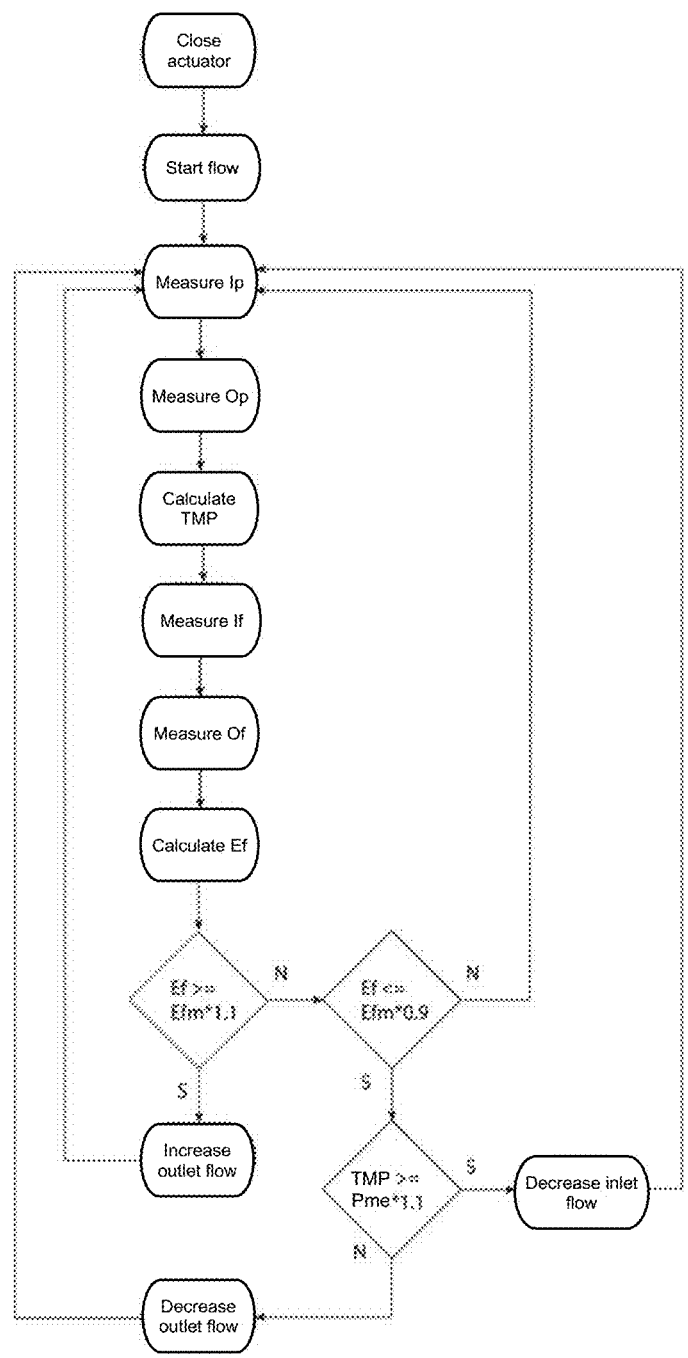
FIG. 5—illustrates the block diagram of a second embodiment of the blood recovery process according to the present invention.
Figure 6:
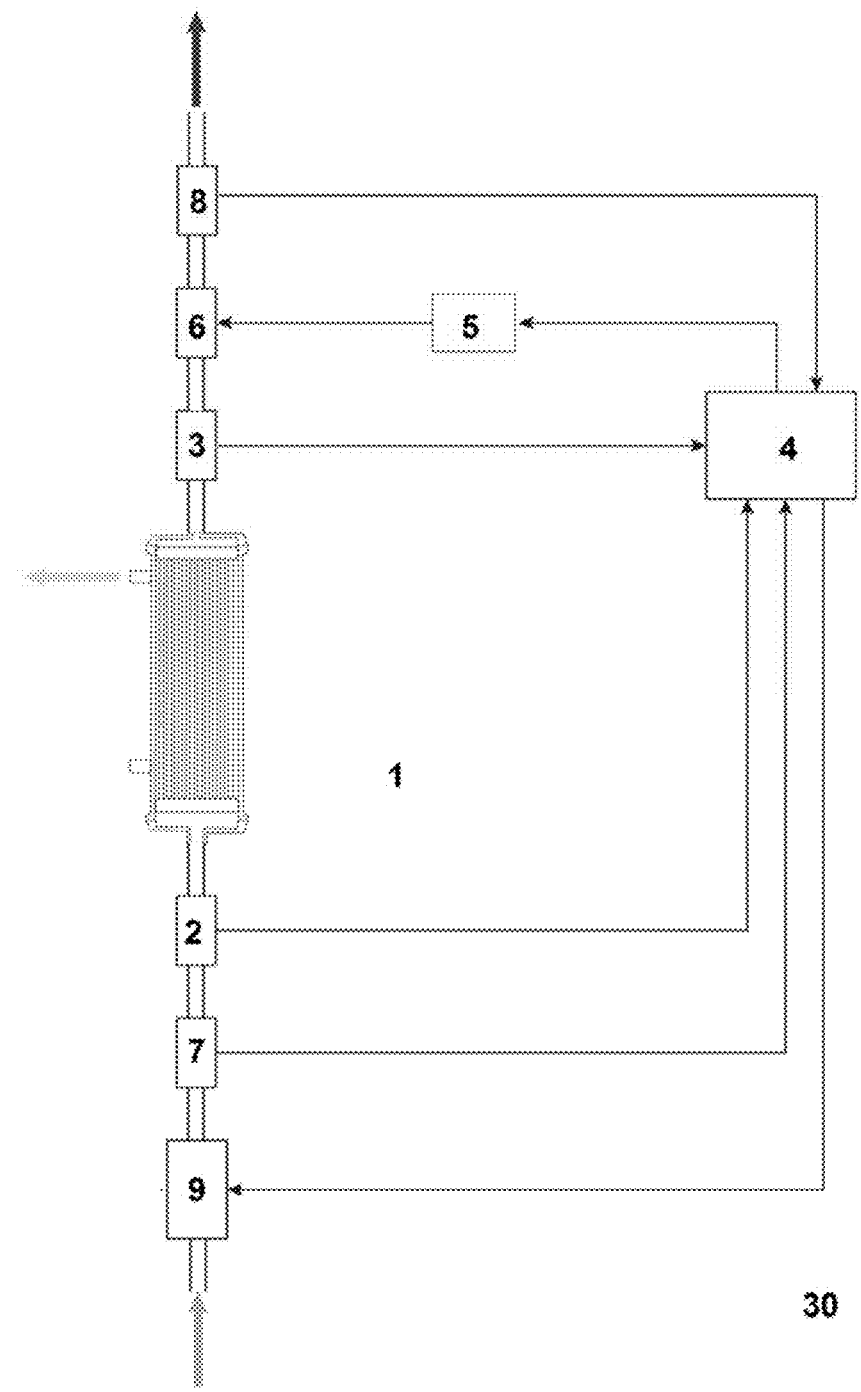
FIG. 6—illustrates a scheme of a second embodiment of the equipment according to the present invention.

Furthermore, a more complete control of the entire system can be obtained by the process illustrated in FIG. 5 and the equipment (30) is illustrated in FIG. 6, wherein the equipment (30) comprises the same components as the equipment (20), as well as the arrangement thereof. In addition, the equipment (30) comprises a pump (9) connected to the flow sensor (7), said pump (9) being connected to the CPU (4).

Another way to achieve the same operating result is described above by a simpler equipment that uses a valve (11), herein called "Physiovalve", provided on the filter outlet. This valve (11) has characteristics that allows it to carry out all the flow control and TMP performed by the above described systems, automatically and without the need for complex systems, since it mechanically implements the control algorithms above revealed.

Said valve (11) comprises a membrane made of flexible and impermeable material, molded in the format of a sphincter and assembled inside a hermetically sealed rigid casing. It is molded in the closed position and it is forced to open by the time it receives the flow at its inlet. However, the opening is proportional to the pressure applied at the inlet, because, when the opening occurs, it compresses the air contained within the outer space, between the membrane and the casing, making pressure within this compartment. Thereby, the valve (11) opens until the pressure in the outer compartment equals the inlet pressure. Due to this characteristic, the valve (11) will act as a flow limiter. In addition, when injecting air inside the outer compartment of the valve (11), an opening pressure can be set, since the valve will only open when the inlet pressure is greater than the pressure inside the outer compartment. Therefore, if a so-called "Physiovalve" is installed and adjusted with an opening pressure lower than the filter's TMP at the hemoconcentrator outlet, the TMP will be forced to increase, since only flow through the valve will exist when the pressure at its inlet is greater than the adjusted pressure.

Figure 7:
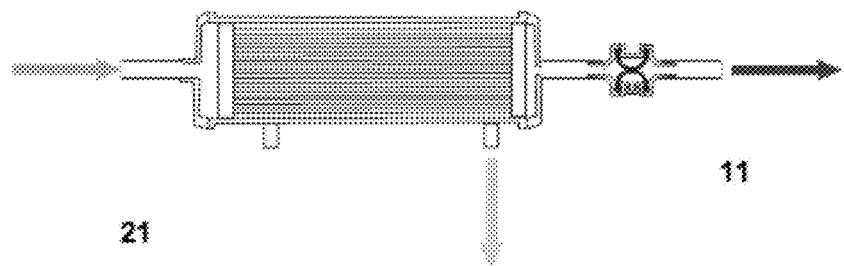
FIG. 7—illustrates a third embodiment of the blood recovery equipment according to the present invention.

FIG. 7 illustrates this construction that works based on the fact that, at the beginning of the process, the system must be filled with serum and the "Physiovalve" (11) is closed due to the pressure inside the outer compartment. Therefore, when the blood flow is started, blood begins to enter the filter (1) and accumulates inside it. Meanwhile, the serum that filled the filter (1) is pushed by the blood that enters and starts to leave the membrane pores, until the filter (1) is completely filled with blood. At this moment, the internal pressure inside the filter (1) starts to increase when the pressure at the valve (11) inlet exceeds the adjusted pressure. The valve (11) begins to open gradually until the inlet pressure, imposed by the blood flow, equals the pressure inside the outer compartment of the valve (11). From this point on, since there is no recirculation and the incoming blood is always in the same condition, the system is in balance until the end of the process. An interesting detail is that the opening of the valve (11) depends on the pressure at its inlet, therefore, it varies according to the flow and also to the hematocrit, since the higher the hematocrit, the greater the viscosity of the blood and, consequently, the greater the pressure generated by the flow. In this way, the opening of the valve (11) is proportional to the flow and the hematocrit. Thus, "Physiovalve" offers additional resistance at the filter outlet, being able to increase filtration efficiency while keeping the TMP within the safety limit in a fully automatic manner. Just being required that the pressure in the valve and the flow be adjusted according to the chosen hemofilter and the "Physiovalve" be designed so as its maximum opening is obtained with a pressure that generates a TMP less than the maximum TMP.

In an example of evaluation of this system, one filter F50S from company Fresenius, provided with "Physiovalve" at the outlet, with an opening pressure set to 100 mmHg and inflow of 300 mL/min has been used. With these parameters, a 65.43% filtration efficiency, compared to 5% with the same filter, with the same flow and blood under the same conditions, but without said "Physiovalve", has been achieved.

Additionally, using the equipment (21) of FIG. 7, in the same filter, for each combination of flow and opening pressure, the system reaches a certain final hematocrit. In the case of the example cited above, for example, the final hematocrit was around 48% regardless of the initial hematocrit. This result is explained by the fact that, considering the same flow, the lower the hematocrit, the lower the pressure generated by the flow and, therefore, the smaller the valve opening (11) and the greater the filtration efficiency. Thus, the valve (11) automatically regulates its opening in order to obtain a certain final hematocrit. This characteristic is very interesting as it does not require any special control by the user, not even prior knowledge of the initial hematocrit of the blood that will be processed. In addition, due to such a feature, one can promote an additional dilution of the blood to be recovered before the procedure, since the blood will thereby be "washed" during the process. In doing so, while increasing the hematocrit of the processed blood, it is possible to remove impurities from the blood, such as urea, creatinine, inflammatory mediators, etc., whereas preserving essential blood components, such as red blood cells, platelets and proteins.

Figure 8:
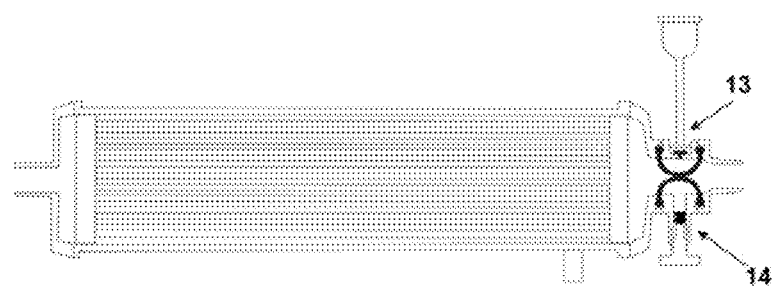
FIG. 8—illustrates a fourth embodiment of the blood recovery equipment according to the present invention.

In order to allow a more practical adjustment of the system parameters, the equipment (22) shown in FIG. 8 can be used. With this configuration, it is possible to adjust, manually or remotely, the opening pressure of the "Physiovalve" (11) through a small piston (14) installed in the casing thereof. The opening pressure must be adjusted before starting the process. The pressure sensor (13) embedded in the "Physiovalve" casing serves to ensure a precise adjustment and also to monitor the pressure at the outlet of the filter (1) during the blood recovery process, if necessary.

Figure 9:
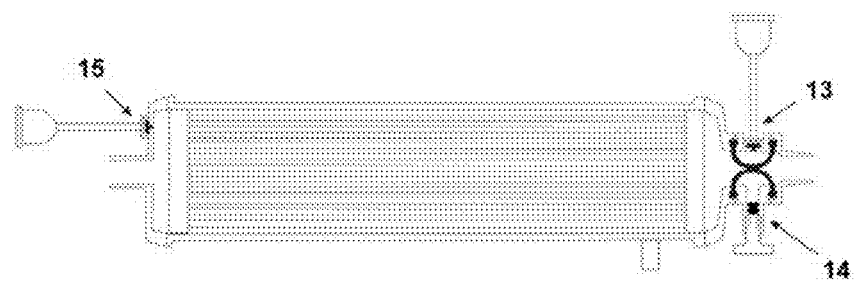
FIG. 9—illustrates a fifth embodiment of the blood recovery equipment according to the present invention.

Additionally, with the purpose of obtaining greater control of the process, the equipment configuration (23) illustrated in FIG. 9 is especially suitable. With this equipment (23), it is possible to adjust, manually or remotely, the opening pressure of the "Physiovalve" (11) through the small piston (14) installed in its casing, and to monitor the pressure inside and at the filter inlet, so that one can calculate TMP in real-time during the process. With this configuration, the opening pressure must be adjusted before the process starts and the transducer serves as a guarantee of its precise adjustment and also to monitor the pressure at the filter outlet during the process. The pressure sensor (15) at the inlet serves to measure the filter inlet pressure, aiming at allowing the calculation of TMP, during the process.

Figure 10:
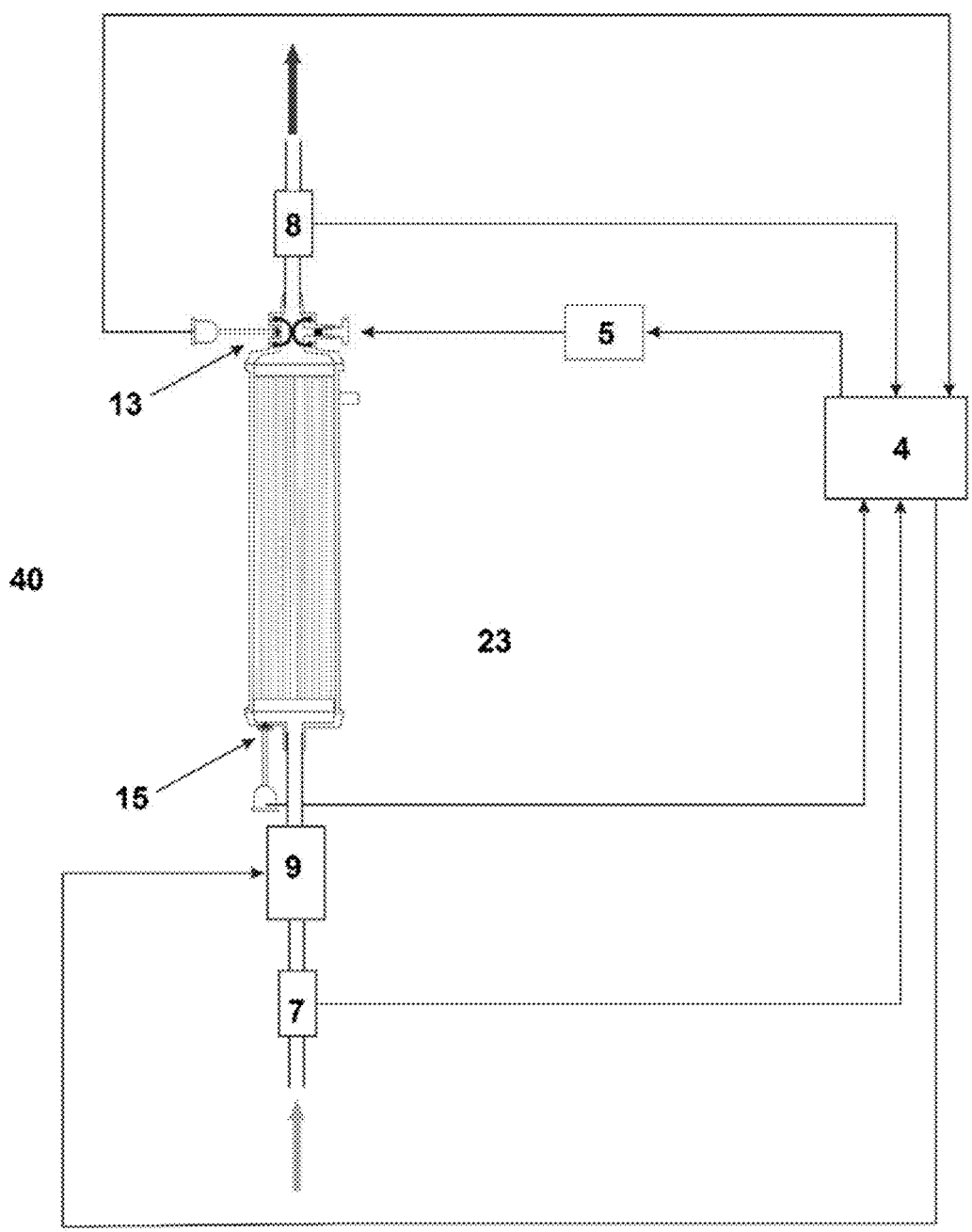
FIG. 10—illustrates a sixth embodiment of the blood recovery equipment according to the present invention.

Also, when installing air flow sensors at the filter inlet and outlet, one can calculate the TMP besides the filtration efficiency of the system in real-time. FIG. 10 illustrates this possibility, by means of a control equipment that sets the system parameters and monitors the whole process, while the valve (11) "Physiovalve" automatically adjusts the opening to obtain the desired result. Thus, the dedicated software is much simpler and the result more reliable, as there is no need to constantly set the parameters of the "Physiovalve". The equipment (40), illustrated by FIG. 10, comprises a hemofilter (23) having, at one end thereof, an inlet pressure sensor (15) and an outlet pressure sensor (13), said pressure sensor (15) is located at the inlet portion of the hemofilter (23) and said pressure sensor (13) is located at the outlet of the hemofilter (23), the equipment (40) comprising a pump (9) connected upstream the hemofilter (23), an inlet flow sensor (7) and an outlet flow sensor (8), the outlet flow sensor (7) is connected upstream of the pump (9), and the flow sensor (8) is connected downstream of the pressure sensor (13). Pressure sensors (13) and (15), flow sensors (7 and 8) and the pump (9) are interconnected to a CPU (4), wherein the CPU (4) is connected to an actuator (5) that adjusts the opening pressure of the valve (11).

Figure 11:
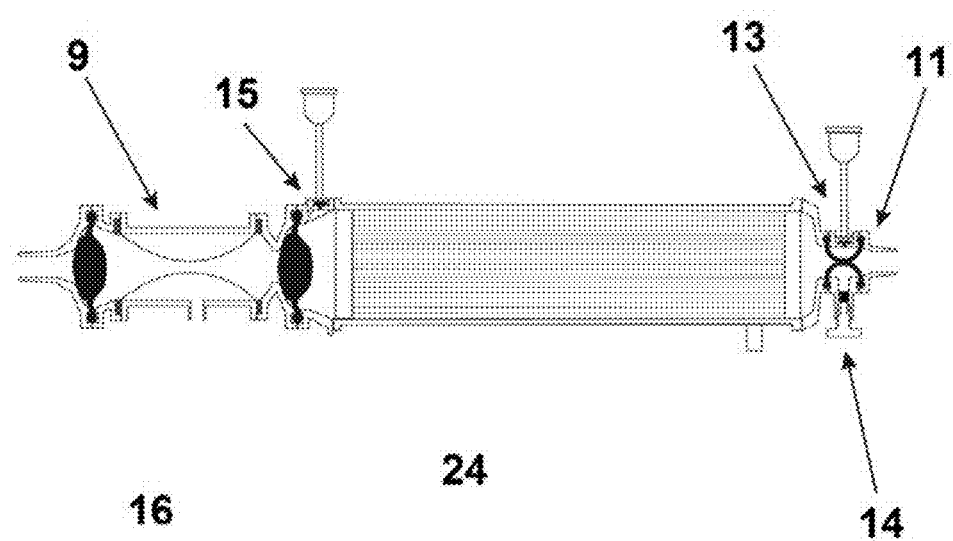
FIG. 11—illustrates a seventh embodiment of the blood recovery equipment according to the present invention.
Figure 12:
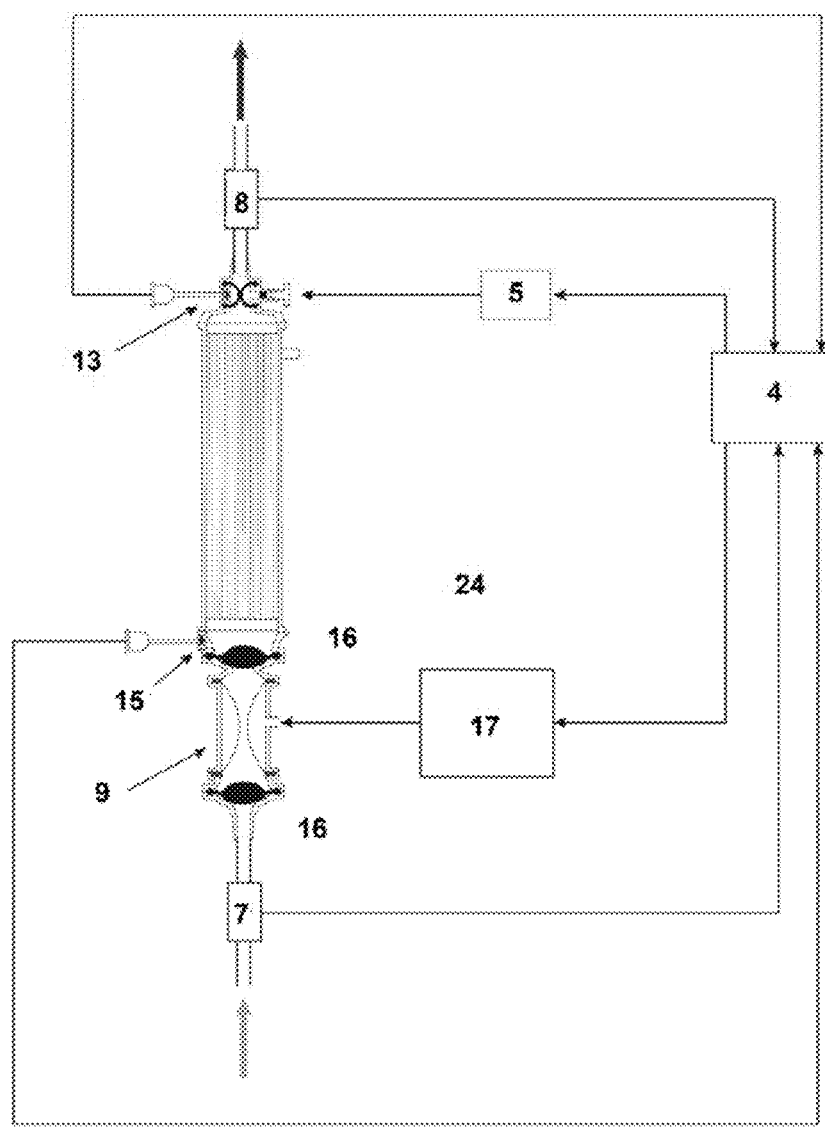
FIG. 12—illustrates an eighth embodiment of the blood recovery equipment according to the present invention.

FIG. 11 illustrates a more complete embodiment of the equipment of the present invention, which comprises, coupled to the hemofilter (1), a physiological pump (9) with a low hemolysis index. This pump (9), as the "Physiovalve", is the object of another patent application of the same applicant. Said pump (9) comprises a flexible and impermeable membrane installed inside a hermetically sealed rigid casing having "Cartwheel"-like valves (16) at the inlet and outlet, being especially indicated for pumping blood due to its low hemolysis index. Pumping is achieved through an outer driver (17) that cyclically injects and sucks air or liquid into the compartment formed between the membrane and the outer pump casing, through a side connector. The complete system is illustrated in FIG. 12, wherein the equipment (50) comprises a hemofilter (1) having, at one end thereof, an inlet pressure sensor (15) and an outlet pressure sensor (13), said pressure sensor (15) is located at the inlet portion of the hemofilter (24) and said pressure sensor (13) is located at the outlet of the hemofilter (24), the equipment (50) comprising a pump (9) connected upstream of the hemofilter (24), an inlet flow sensor (7) and an outlet flow sensor (8), the outlet flow sensor (7) is connected upstream of the pump (9), and the flow sensor (8) is connected downstream of the pressure sensor (13). The pump (9) is connected to the outer driver (17). Pressure sensors (13) and (15), flow sensors (7 and 8) and the outer driver (17) are interconnected to a CPU (4), wherein the CPU (4) is connected to an actuator (5) that controls the opening pressure of the valve (11).

Figure 13:
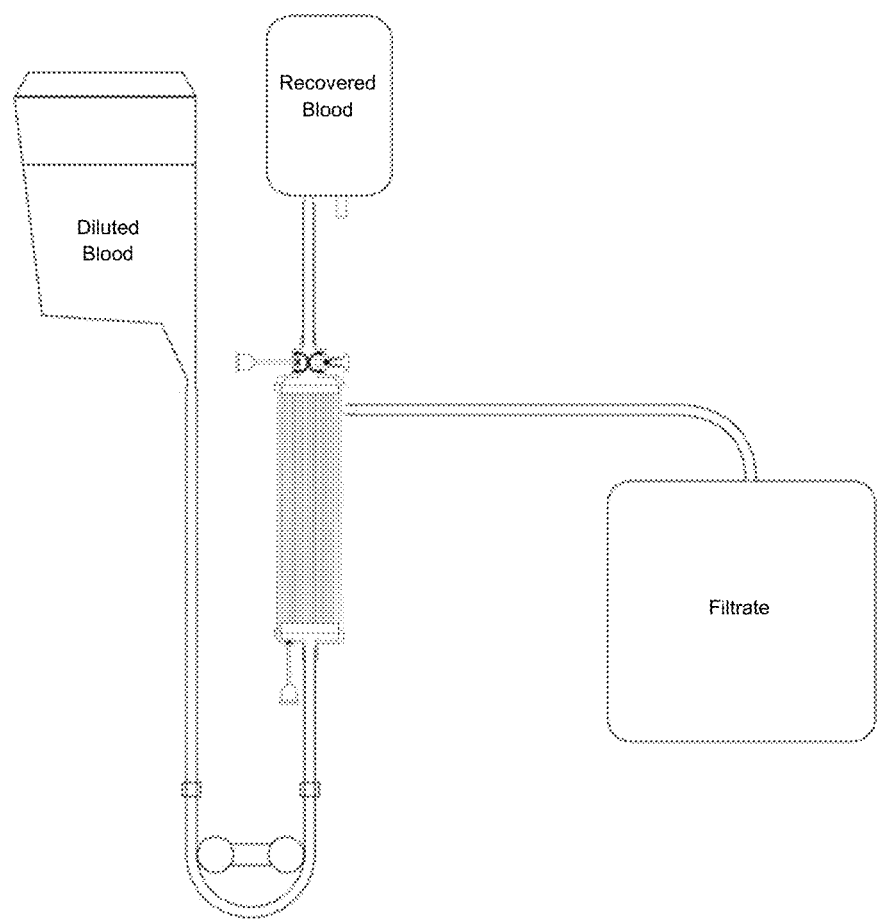
FIG. 13—illustrates a ninth embodiment of the blood recovery equipment according to the present invention.
Figure 14:
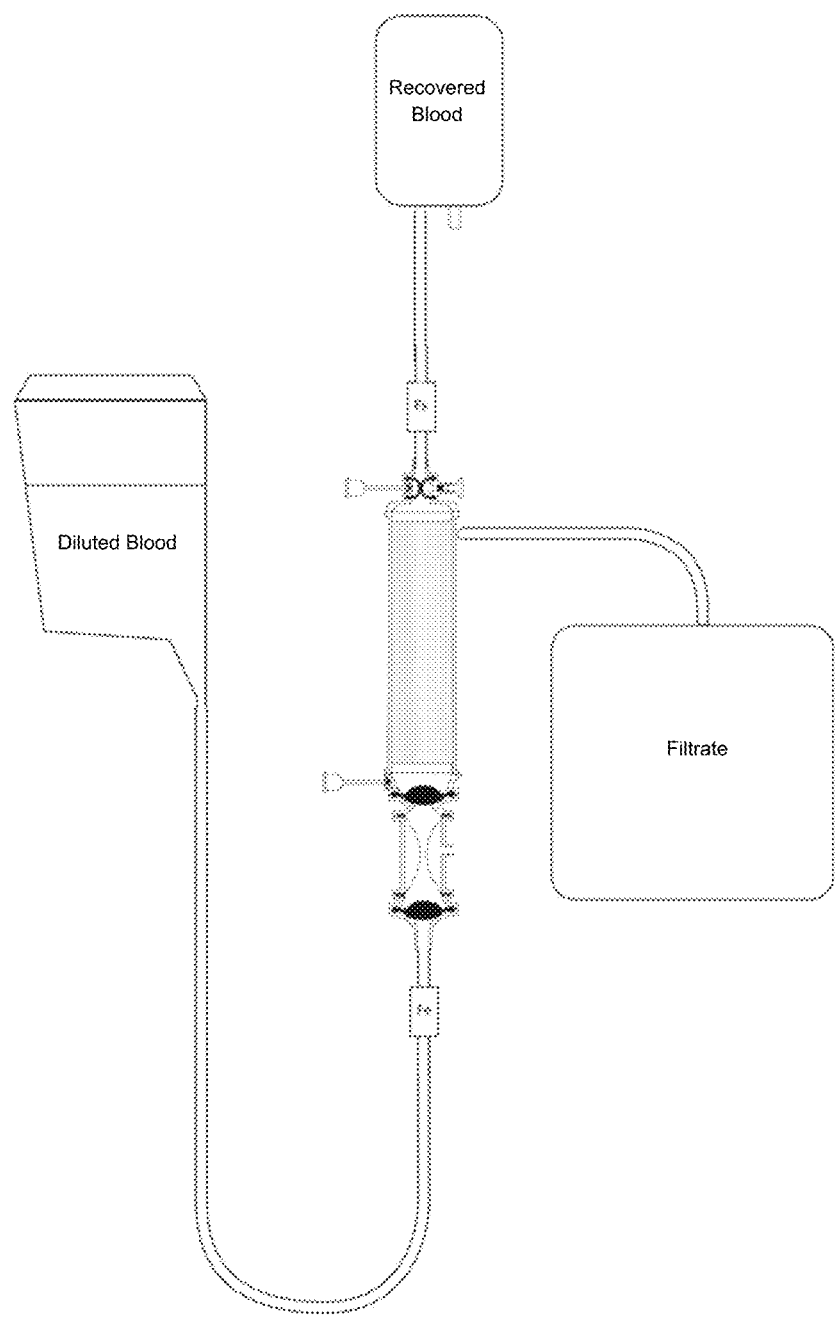
FIG. 14—illustrates a scheme of a first embodiment of the equipment according to the present invention.

As a general illustration, FIG. 13 represents the assembly of the simplified circuit for blood recovery in accordance with the present invention, while FIG. 14 represents the assembly of the complete circuit for blood recovery in accordance with the present invention.

According to said FIGS. 13 and 14, it is observed that the process and equipment of the present invention provide high filtration efficiency at low flow rates and with low hemolysis. These characteristics make the present invention suitable for recovering blood after surgery, but also, with appropriate adjustments, for use in hemodialysis or hemofiltration in general.

Those skilled in the art will appreciate that, when the present invention is used for hemodialysis, due to high system efficiency, one may perform this procedure at low flow rates and high efficiency, thus reducing the required amount of hemodialysis solution and the total number of times the blood passes through the hemofilter, which generates less hemolysis and allows using a simpler and smaller equipment. These advantageous technical effects are achieved due to the low volume of hemodialysis solution required for the procedure, eliminating the realization of dilution of the hemodialysis concentrate with sterile water, as it happens in prior art systems. A pre-diluted solution may be used, thus eliminating the water treatment system and the currently existing dilution system in hemodialysis machines of the state of the art.

It should also be noted that, although in the hemodialysis process there is blood recirculation and the hematocrit varies over the procedure, as the "Physiovalve" automatically regulates the resistance in the line as a function of the inlet pressure, there is no risk of breaking the fibers, because when the hematocrit increases, the "Physiovalve" opens, decreasing the resistance of the line and, thus, reducing the pressure. Accordingly, hemodialysis becomes safer, more practical and much more efficient when compared to the processes of the state of the art.

The benefits of the blood recovery process and equipment according to the present invention are countless. As an exemplary citation, a typical hemodialysis session currently lasts an average of 4 hours. The blood flow used is 500 mL/min, with an average filtration efficiency of 5%. Thus, during the hemodialysis session, blood circulates 17 to 20 times through the hemofilter, and around 15 mL/min of filtrate is removed, using 100 to 120 liters of hemodialysis solution.

In order to obtain the same hemodialysis results with the process and equipment of the present invention, only a flow around 30 mL/min would be needed. In these circumstances, the patient's blood would circulate only 1, 2 times through the hemofilter and only 6 to 8 liters of hemodialysis solution would be required. Obviously, this procedure would reduce drastically the blood damage, which increase the survival and quality of life of patients and would also allow hemodialysis to be performed in simpler facilities, since there would be no need for all currently existing infrastructure for water treatment and equipment would also be much simpler and smaller.

It is further appreciated that with the process and equipment of the present invention, a drastic reduction in the hemodialysis session time is likely to occur, which would bring numerous benefits for patients and the health system. In this regard, studies are being carried out to determine such feasibility of the invention.

Nevertheless, it is known that as the efficiency of the process and equipment of the present invention is much greater than that obtained by traditional processes and equipment, it would be possible to use smaller and therefore cheaper hemofilters, and still get better results than those currently obtained. This would make it possible to definitively cease the usual reuse of dialyzers, which would also imply a reduction in the labor, materials and infrastructure presently required for dialyzer reprocessing, in addition to increasing the safety of the procedure for patients and health care professionals.

In the claims:

1. A residual blood collection and recovery system for an extracorporeal circulation circuit, comprising:
    a hemofilter provided with hollow fibers, an inlet end, and an outlet end;
    a pump connected upstream of the hemofilter;
    an inlet flow sensor connected upstream of the pump;
    an inlet pressure sensor connected to the inlet end of the hemofilter;
    a flow-limiting valve disposed in the outlet end of the hemofilter,
        wherein the flow limiting valve comprises a flexible membrane molded in a sphincter format,
        wherein the flexible membrane is assembled inside a hermetically sealed rigid casing such that the flexible membrane divides an inner pathway of the flow limiting valve and is provided between a compartment filled with compressed air and a blood flow compartment,
        wherein the flow limiting valve is configured to transition from a closed position to an open position when a pressure of the blood flow leaving the hemofilter corresponds to an opening pressure of the flow limiting valve,
    wherein the flow-limiting valve mechanically and automatically regulates a resistance in a line as a function of the flow-limiting valve inlet pressure,
    wherein an automatic regulation includes a mechanical opening and closing of the membrane of the flow-limiting valve and wherein the automatic regulation is proportional to a flow in the line and a hematocrit;
    an actuator in fluid communication with the compartment filled with compressed air of the flow limiting valve;
    an outlet pressure sensor arranged in the hermetically sealed rigid casing of the flow limiting valve;
    an outlet flow sensor connected downstream of the flow limiting valve; and
    a computer processing unit (CPU) interconnected with the pump, the inlet flow sensor, the outlet flow sensor, the inlet pressure sensor, the outlet pressure sensor, and the actuator,
    wherein the CPU is configured to:
        drive the actuator for controlling the opening pressure of the flow limiting valve,
        continuously calculate a transmembrane pressure and a filtration efficiency, and
        maintain a transmembrane pressure at a magnitude lower than a maximum transmembrane pressure supported by the hemofilter hollow fibers.

2. The system, according to claim 1, further comprising:
    a piston installed in a casing of the flow-limiting valve to adjust an opening pressure of the membrane thereof at a beginning of an extracorporeal circulation process.

3. The system according to claim 2,
    wherein a pressure sensor embedded in the inlet end of the hemofilter measures the filter inlet pressure, together with the outlet pressure sensor, to allow the CPU to calculate the transmembrane pressure during the extracorporeal circulation process.

4. The system, according to claim 1, further comprising a pump, disposed upstream of the hemofilter equipped with a flexible and impermeable membrane installed inside a hermetically sealed rigid casing having cartwheel valves at the inlet and outlet, a pumping being provided through an outer driver that cyclically injects and sucks air or liquid into the compartment formed between said membrane and said outer pump casing, through a side connector.

5. The system, according to claim 2, further comprising a pump, disposed upstream of the hemofilter equipped with a flexible and impermeable membrane installed inside a hermetically sealed rigid casing having cartwheel valves at the inlet and outlet, a pumping being provided through an outer driver that cyclically injects and sucks air or liquid into the compartment formed between said membrane and said outer pump casing, through a side connector.

6. The system according to claim 1,
    wherein a pressure sensor embedded in the inlet end of the hemofilter measures the filter inlet pressure, together with the outlet pressure sensor, to allow the CPU to calculate the transmembrane pressure during the extracorporeal circulation process.

* * * * *